United States Patent
Minami et al.

(10) Patent No.: US 8,544,322 B2
(45) Date of Patent: Oct. 1, 2013

(54) JAW MOTION MEASURING SYSTEM

(75) Inventors: Ichiro Minami, Tokyo (JP); Teruyasu Nakamura, Tokyo (JP); Yoshimasa Igarashi, Sagamihara (JP); Tetsu Nemoto, Kanazawa (JP)

(73) Assignee: National University Corporation Tokyo Medical and Dental University (JP)

( * ) Notice: Subject to any disclaimer, the term of this patent is extended or adjusted under 35 U.S.C. 154(b) by 182 days.

(21) Appl. No.: 13/203,272

(22) PCT Filed: Feb. 25, 2010

(86) PCT No.: PCT/JP2010/052974
§ 371 (c)(1),
(2), (4) Date: Nov. 15, 2011

(87) PCT Pub. No.: WO2010/098388
PCT Pub. Date: Sep. 2, 2010

(65) Prior Publication Data
US 2012/0048013 A1   Mar. 1, 2012

(30) Foreign Application Priority Data
Feb. 27, 2009   (JP) .................................. 2009-047257

(51) Int. Cl.
*A61B 1/24* (2006.01)
(52) U.S. Cl.
USPC ....................................................... 73/379.01
(58) Field of Classification Search
USPC .......................................... 73/379.02–379.05
See application file for complete search history.

(56) References Cited

FOREIGN PATENT DOCUMENTS

| JP | 63-061121 | 3/1988 |
|----|-----------|--------|
| JP | 10-124254 | 5/1998 |
| JP | 2008-18010 | 1/2008 |
| JP | 2008-018094 | 1/2008 |
| JP | 2008-307207 | 12/2008 |

OTHER PUBLICATIONS

Description of Product Nasohekisa manufactured by GC Corporation, http://www.gcdental.co.jp/product/pdf/nasohekisa.pdf, Oct. 4, 2004.
Kunitaka Isaji et al., "Shika Ryoiki ni Okeru Kasokudo Sensor no Oyo", Chiiki iryo, 2002, special extra issue, 604-606.
Ivica Pelivan et al, Tri-axial Accelerometric Analysis of Dynamic Patterns of Mandibular Movements, International Poster Journal of Dentistry and Oral Medicine [online], 2007, vol. 1.2, No. 2, Poster 360, [retrieval date May 27, 2010], Internet (URL:http://ipj.quintessenz.de/index.php?content=awards&doc=poster&select=360).

*Primary Examiner* — Jewel V Thompson
(74) *Attorney, Agent, or Firm* — Berliner & Associates

(57) ABSTRACT

There is provided a jaw motion measuring system that can attach a simple detector and can accurately carry out measurement of jaw motion. The jaw motion measuring system includes: an acceleration detector having at least an acceleration sensor that senses accelerations of three-axis directions, a flexible wire whose one end is connected to the acceleration sensor, an output terminal that is connected to another end of the flexible wire and outputs acceleration data of the three-axis directions, and an attachment portion that attaches the acceleration sensor to a chin portion of a lower jaw; and a jaw motion measuring device that acquires acceleration data corresponding to jaw motion from the acceleration detector, and carries out correction, with respect to the acquired acceleration data, of errors due to the acceleration sensor, and measures jaw motion expressed by acceleration waveforms.

6 Claims, 13 Drawing Sheets

FIG.8
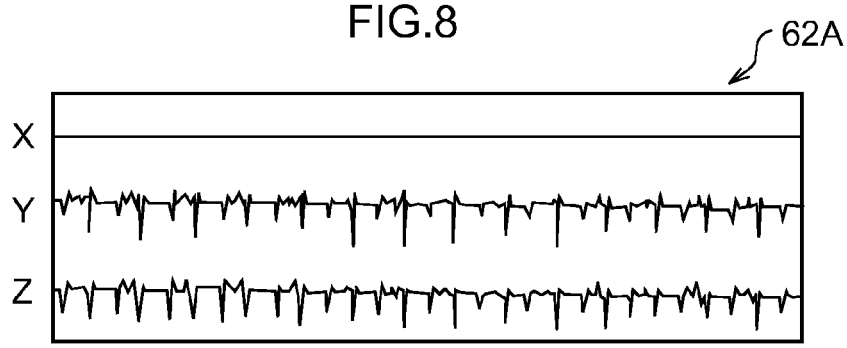
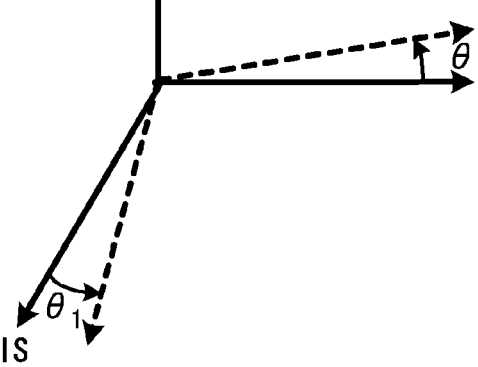
FIG.9A
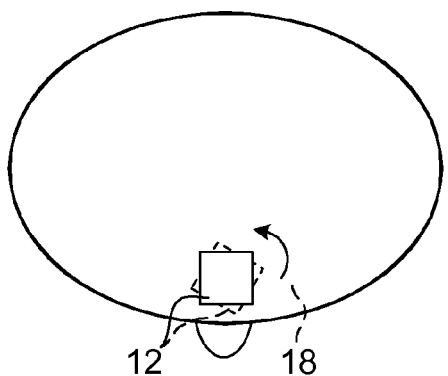
FIG.9B

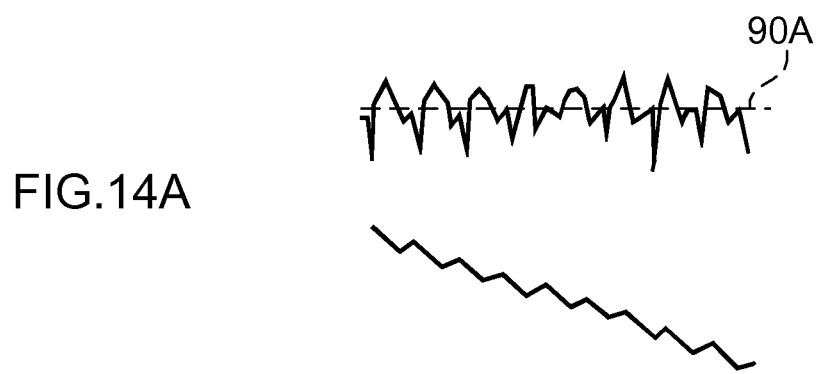
FIG.14A
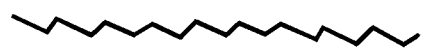
FIG.14B
FIG.14C
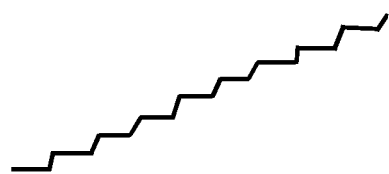

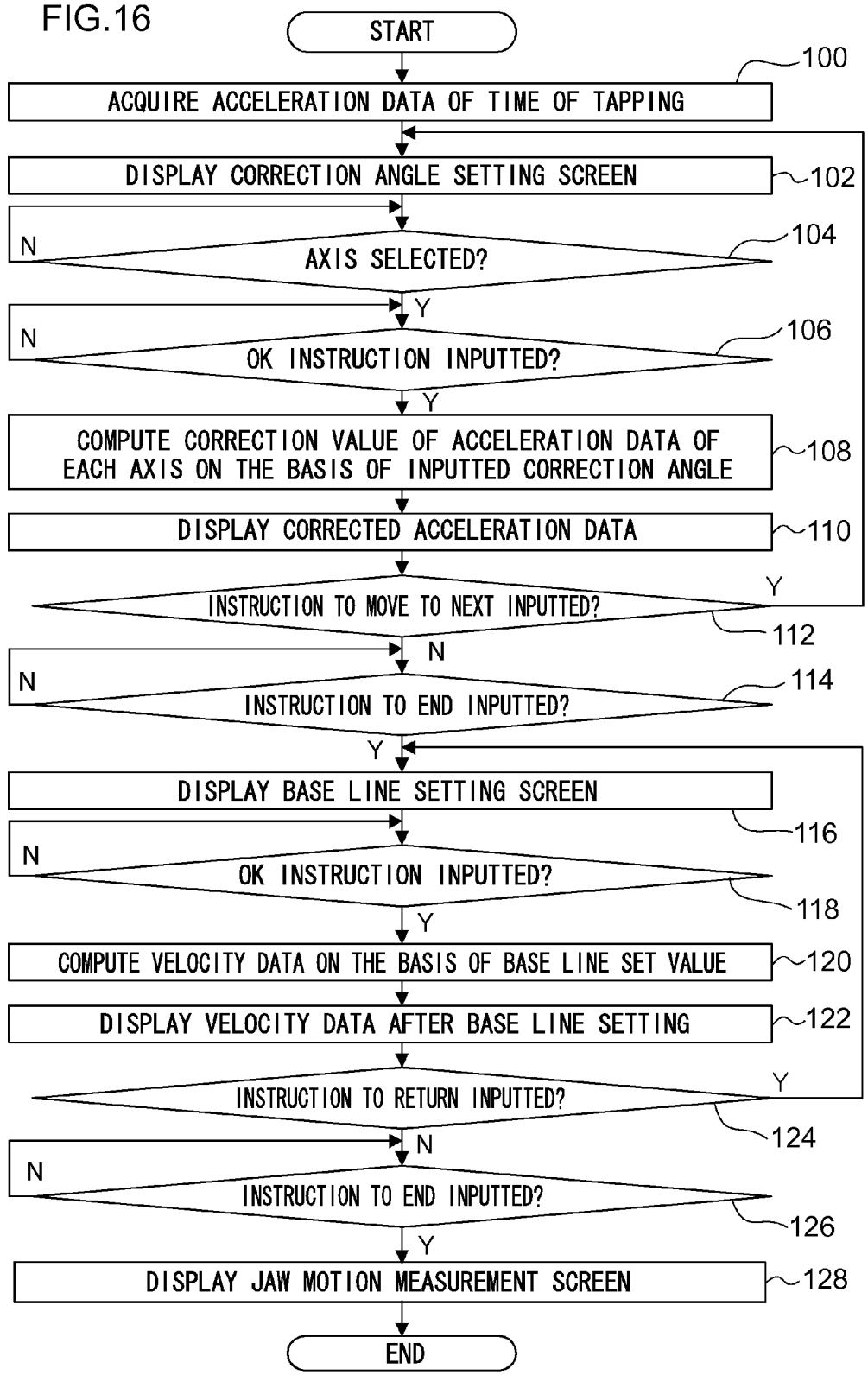

US 8,544,322 B2

JAW MOTION MEASURING SYSTEM

This application is a 371 of PCT/JP2010/052974 Feb. 25, 2010.

TECHNICAL FIELD

The present invention relates to a jaw motion measuring system.

BACKGROUND ART

Jaw motion is classified into rotating motion of the mandibular condyle with the mandibular fossa as a bearing, and gliding motion in which the mandibular condyle moves forward. For example, when the mouth or jaws are opened/closed slightly due to chewing or the like, mainly rotating motion arises. On the other hand, when the mouth or jaws are greatly opened/closed by yawning or the like, not only rotating motion, but gliding motion also arises. Abnormalities of the jaw oral cavity functions, such as mismatching of the occlusion or the like, can be diagnosed from measurements of these jaw motions. In order to carry out appropriate treatment, it is important to accurately measure jaw motion for each subject.

Current, there exist "GNATHO-HEXA" and the like, which is manufactured by GC Corporation, as jaw motion measuring devices that are becoming popular among some clinicians. Refer to www.gcdental.co.jp/product/pdf/nasohekisa.pdf on the Internet. This device attaches, to the patient, a headgear, and an implement that fixes to the row of teeth, and measures three-dimensional motions such as chewing motion, opening/closing motion, and the like. Namely, the relative position of the lower jaw is measured, and jaw motion measurement is carried out. In addition thereto, for example, devices called "kinesiographs" are becoming popular. This is a device that fixes a magnet to the row of teeth of the lower jaw, and three-dimensionally measures jaw motion by capturing magnetism. These two are representative as devices that measure jaw motion in current clinic settings.

Further, in Japanese Patent Application Laid-Open No. 2008-18094 (JP200818094A1) and Japanese Patent Application Laid-Open No. 2008-18010 (JP200818010A1), there are proposed, as techniques that easily carry out jaw motion measurement, various techniques of attaching an acceleration sensor to the chin portion or the like of the lower jaw, and measuring the oral cavity motion of a subject on the basis of the output of the acceleration sensor.

PRIOR ART DOCUMENTS

Non-Patent Documents

Non-Patent Document 1: www.gcdental.co.jp/product/pdf/nasohekisa.pdf on the Internet

Patent Documents

Patent Document 1: Japanese Patent Application Laid-Open No. 2008-18094
Patent Document 2: Japanese Patent Application Laid-Open No. 2008-18010

SUMMARY OF INVENTION

Technical Problem

However, commercially-available jaw motion measuring devices have the problems that they are expensive at several million yen and they lack versatility. Further, there is the problem that the burden on the patient side is great, such as measurement is carried out with the headgear attached to the patient, and the like. Further, the measurement conditions are strict, and a room exclusively used for measurement must be readied, and hospitals into which the devices can be introduces also are limited. On the other hand, with conventional jaw motion measuring devices using an acceleration sensor, there is the concern of picking-up vibrations of the skin or the cord, and further, because there is no reproducibility in the attachment direction, there is the problem that accurate measurement cannot be carried out.

The present invention was made in order to overcome the above-described problems, and an object thereof is to provide a jaw motion measuring system that attaches a simple detector and can carry out measurement of jaw motion accurately. Further, in addition to the above-described object, an object of the present invention is to provide a jaw motion measuring system that is inexpensive and versatile, as compared with commercially-available jaw motion measuring devices.

Solution to Problem

In order to achieve the above-described objects, the invention recited in aspect 1 is a jaw motion measuring system including: an acceleration detector having at least an acceleration sensor that senses accelerations of three-axis directions, a flexible wire whose one end is connected to the acceleration sensor, an output terminal that is connected to another end of the flexible wire and outputs acceleration data of the three-axis directions, and an attachment portion that attaches the acceleration sensor to a chin portion of a lower jaw; and a jaw motion measuring device that acquires acceleration data corresponding to jaw motion from the acceleration detector, and carries out correction, with respect to the acquired acceleration data, of errors due to the acceleration sensor, and measures jaw motion expressed by acceleration waveforms.

The invention of aspect 2 is the jaw motion measuring system of aspect 1, wherein the acceleration sensor is attached to the chin portion of the lower jaw such that an X-axis direction corresponds to a left-right direction, a Y-axis direction corresponds to a front-back direction, and a Z-axis direction corresponds to a vertical direction, and the jaw motion measuring device has a position offset correcting unit that carries out a first correction, that rotates orthogonal coordinates of the acceleration sensor around a Z-axis such that acceleration data of the X-axis direction becomes a minimum, and a second correction, that rotates the orthogonal coordinates of the acceleration sensor around an X-axis such that acceleration data of the Z-axis direction becomes a minimum, and carries out correction, with respect to the acquired acceleration data, of errors due to attachment position offset of the acceleration sensor.

The invention of aspect 3 is the jaw motion measuring system of aspect 2, wherein the jaw motion measuring device further has a display device and a display control device that controls the display device, and the display control device displays, on the display device, acceleration data acquired from the acceleration detector, an axis selection section that selects any of three axes of the acceleration sensor, and an angle setting section that sets a rotation angle around a selected axis, and the position offset correcting unit carries out first correction, that rotates the orthogonal coordinates of the acceleration sensor around the Z-axis selected by the axis selecting section by an angle set by the angle setting section and makes the acceleration data of the X-axis direction be the minimum, and second correction, that rotates the orthogonal coordinates of the acceleration sensor around the X-axis selected by the axis selecting section by an angle set by the angle setting section and makes the acceleration data of the Z-axis direction be the minimum.

The invention of aspect 4 is the jaw motion measuring system of any one of aspects 1 through 3, wherein the jaw motion measuring device further has a base line setting unit that sets a base line for acceleration data acquired from the acceleration detector and prescribes a zero point of an acceleration waveform, so that a velocity waveform, that is obtained by integrating a voltage signal of the Y-axis direction, fluctuates in a definite amplitude range.

The invention of aspect 5 is the jaw motion measuring system of aspect 4, wherein, until a base line is decided upon, the jaw motion measuring device repeatedly carries out a first process, in which the display control device displays, on the display device, acceleration data of the Y-axis direction acquired from the acceleration detector and a base line setting section that sets a base line for the acquired acceleration data, and a second process in which the base line setting unit integrates the acceleration data of the Y-axis direction on the basis of a base line set by the base line setting section, and a third process in which the display control device displays, on the display device, a velocity waveform obtained by integrating the acceleration data of the Y-axis direction, and the jaw motion measuring device sets a base line for the acceleration data, and prescribes a zero point of an acceleration waveform.

The invention of aspect 6 is the jaw motion measuring system of any one of aspects 1 through 5, wherein the acceleration sensor is made to be light-weight and compact, to an extent that skin of the chin portion of the lower jaw is not made to hang downward.

The invention of aspect 7 is the jaw motion measuring system of any one of aspects 1 through 6, wherein the flexible wire is made to be light-weight and is provided with flexibility, to an extent of not causing accelerations that are sensed by the acceleration sensor to fluctuate.

The invention of aspect 8 is the jaw motion measuring system of any one of aspects 1 through 7, wherein the attachment portion has a buffer member that holds the acceleration sensor and absorbs vibrations of skin, and an adhering member that adheres the acceleration sensor to the chin portion of the lower jaw via the buffer member.

Advantageous Effect of Invention

There are the following effects in accordance with the inventions relating to the respective aspects.

In accordance with the invention recited in aspect 1, there is the effect that there can be provided a jaw motion measuring system that can attach a simple detector, and can accurately carry out measurement of jaw motion.

In accordance with the invention recited in aspect 2, there is the effect that errors due to attachment position offset of the acceleration sensor can be corrected.

In accordance with the invention recited in aspect 3, there is the effect that errors, that are due to attachment position offset of the acceleration sensor, can be corrected in real time while looking at the display screen.

In accordance with the invention recited in aspect 4, there is the effect that the base line can be set and the zero point of the acceleration waveform can be prescribed.

In accordance with the invention recited in aspect 5, there is the effect that the base line can be set and the zero point of the acceleration waveform can be prescribed in real time, while looking at the display screen.

In accordance with the inventions recited in aspects 6, 7, 8, there is the effect that generation of noise due to vibrations of the acceleration sensor can be suppressed.

BRIEF DESCRIPTION OF DRAWINGS

FIG. 8 is a drawing showing a screen that displays acceleration data after correction.

FIG. 9A is a drawing that explains the meaning of first correction.

FIG. 9B is a drawing that explains the meaning of first correction.

FIG. 14A is a drawing showing the relationship between the position of the base line and a velocity waveform.

FIG. 14B is a drawing showing the relationship between the position of the base line and a velocity waveform.

FIG. 14C is a drawing showing the relationship between the position of the base line and a velocity waveform.

FIG. 16 is a flowchart showing a processing routine of a jaw motion measuring program.

DESCRIPTION OF EMBODIMENTS

Hereinafter, an example of an embodiment of the present invention is described in detail with reference to the drawings.
<Jaw Motion Measuring Device>
(Overall Device Configuration)

Figure 1:
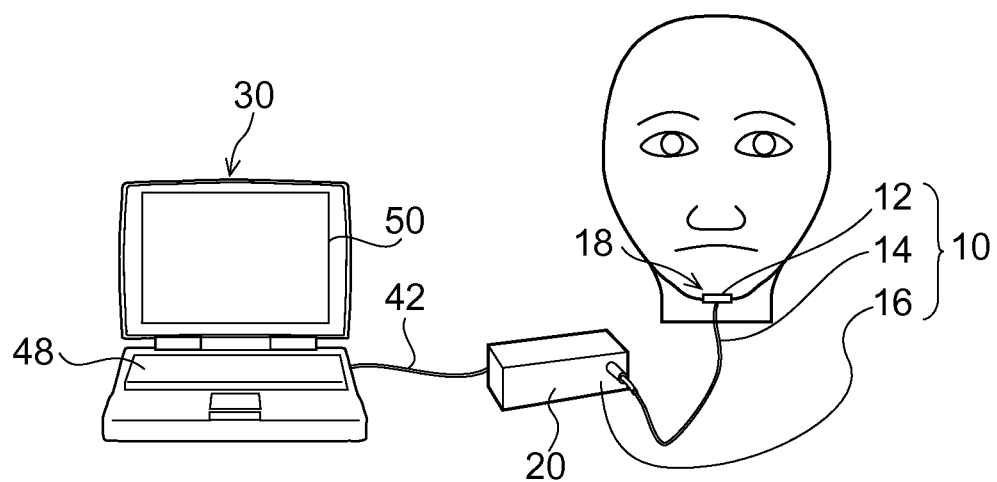
FIG. 1 is a schematic drawing showing the configuration of a jaw motion measuring system relating to an embodiment of the present invention.

FIG. 1 is a schematic drawing showing the configuration of a jaw motion measuring system relating to an embodiment of the present invention. As shown in FIG. 1, the jaw motion measuring system is configured to include an acceleration detector 10, an interface device 20 that analog/digital converts the output of the acceleration detector 10, and a jaw motion measuring device 30 that is connected to the acceleration detector 10 via the interface device 20. The acceleration detector 10 has an acceleration sensor 12 that senses accelerations in three-axis directions, a flexible wire 14 whose one end is connected to the acceleration sensor 12, and a connector 16 that is connected to the other end of the flexible wire 14. The connector 16 is connected to the interface device 20. The acceleration sensor 12 is attached to a chin portion 18 of the lower jaw by using an attachment member that is described later. The acceleration detector 10 senses, by the acceleration sensor 12, voltage signals (hereinafter called accelerations or acceleration data for convenience) that correspond to the accelerations in the three-axis directions. The sensed voltage signals are inputted to the interface device 20 via the flexible wire 14 and the connector 16, and are converted from analog signals into digital signals. The acceleration data that have been converted into digital signals are inputted to the jaw motion measuring device 30. The jaw motion measuring device 30 acquires the acceleration data corresponding to the jaw motion from the acceleration detector 10, and carries out correction, on the acquired acceleration data, of errors due to the acceleration sensor 12, and measures the jaw motion expressed by the acceleration waveforms.

(Acceleration Sensor Periphery)

Figure 2:
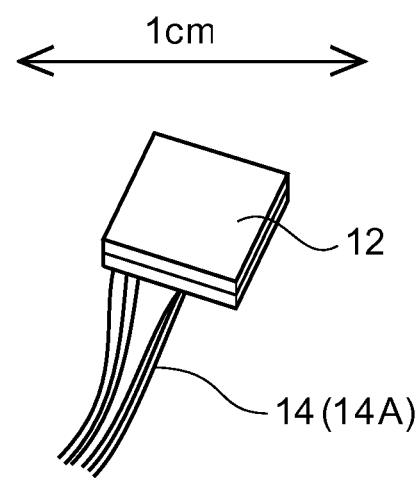
FIG. 2 is a schematic drawing showing the configuration of the peripheral portion of an acceleration sensor.

FIG. 2 is a schematic drawing showing the configuration of the peripheral portion of the acceleration sensor. As shown in FIG. 2, a three-axis acceleration sensor, that is light-weight and compact of a size of around 5 mm×5 mm, is suitably used as the acceleration sensor 12. The light-weight and compact acceleration sensor 12 does not cause the skin of the chin portion 18 of the lower jaw to hang downward, and therefore, the occurrence of noise due to vibrations of the acceleration sensor 12 is suppressed. In the present embodiment, a chip, that is removed from a sensor board of a commercially-available acceleration sensor (the three-axis acceleration sensor "AS-3ACC") manufactured by Asakusa Giken), is used as the acceleration sensor 12.

Further, a flexible wire, that is light-weight and has high flexibility to the extent that it can be bent-over, is suitably used as the flexible wire 14. The flexible wire 14 that is light-weight and has high flexibility does not cause the voltage signals, that are sensed by the acceleration sensor 12, to fluctuate. The flexible wire 14, in which plural thin wires 14A are bundled in accordance with the number of lead terminals of the acceleration sensor 12, is used in the present embodiment. In FIG. 2, six of the thin wires 14A are bundled. The respective thin wires 14A are electric wires that are covered by insulating covering films, and the covering films at the end portions are removed, and the thin wires 14A are directly soldered to the lead terminals of the acceleration sensor 12. An electric wire, that has a diameter of 0.05 mm and that is covered by foam PTFE manufactured by Junkosha Inc., is used as the thin wire 14A in the present embodiment. PTFE is tetrafluoroethylene resin, and is so-called TEFLON™.

(Jaw Motion Measuring Device)

Figure 3:
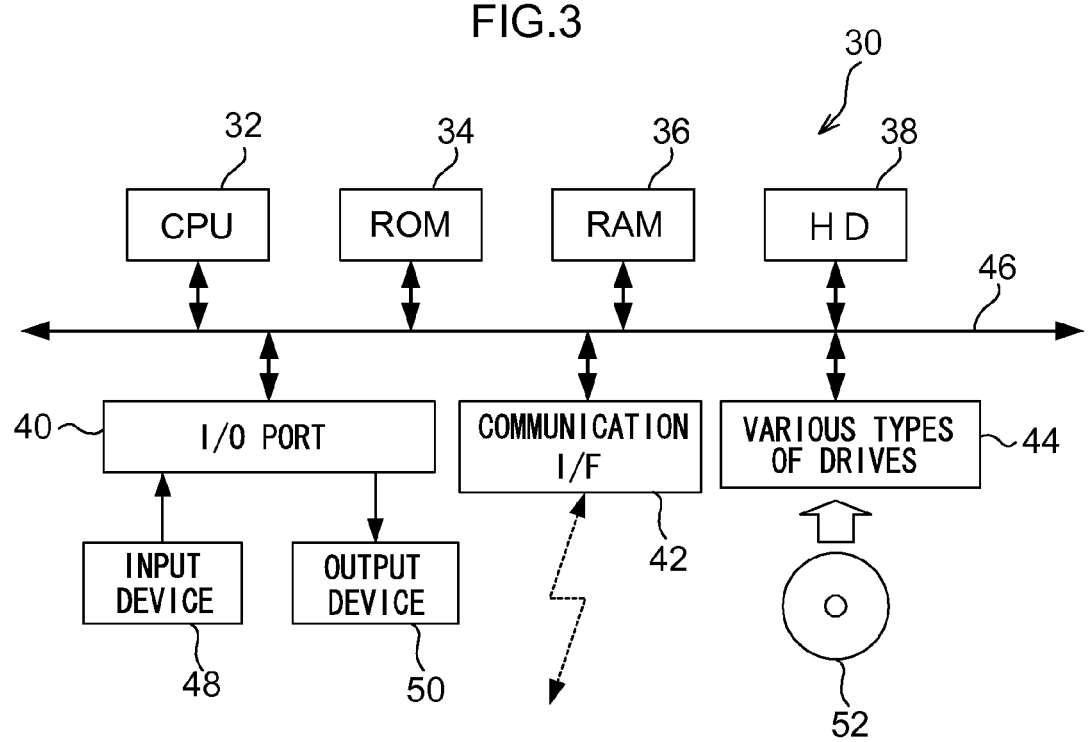
FIG. 3 is a block diagram showing the configuration of a jaw motion measuring device.

FIG. 3 is a block diagram showing the configuration of the jaw motion measuring device. The jaw motion measuring device 30 is configured by, for example, a computer in which a jaw motion measuring program is installed, and peripheral devices thereof. As shown in FIG. 3, the jaw motion measuring device 30 has a CPU (Central Processing Unit) 32 that carries out control of the device overall and various types of computation, a ROM (Read Only Memory) 34 that stores various types of programs such as OS (Operating Systems) and the like, a RAM (Random Access Memory) 36 that is used as a work area at the time of executing programs, a hard disk (HD) 38 that stores various types of information, an input/output (I/O) port 40, a communication interface (I/F) 42, and various types of drives 44. These respective portions are connected to one another by a bus 46.

An input device 48 such as a keyboard and a mouse or the like, and a display device 50 such as a display or the like, is connected to the I/O port 40. The communication I/F 42 carries out transmission and receipt of various types of information to and from the exterior via a wired or wireless communication line. Further, in the present embodiment, the communication I/F 42 is wire-connected to the interface device 20 by a cable, and the digital signals (acceleration data) corresponding to the voltage signals outputted from the acceleration detector 10 are inputted. The various types of drives 44 are devices that can read-in data from computer-readable portable storage media 52, such as flexible disks, magneto-optical disks, CD-ROMs and the like, and can write data thereto.

The jaw motion measuring program is read from the portable storage medium 52, and is stored in the ROM 34 or the hard disk 38. Or, the jaw motion measuring program may be transferred via the internet, received by the communication I/F 42, and stored in the ROM 34 or the hard disk 38. Further, a database region (not illustrated) for storing various types of databases, is provided in the hard disk 38, and various types of databases for diagnosis are stored therein.

The CPU 32 reads-out the program from the ROM 34 or the hard disk 38, and loads the program into the RAM 36. Then, the loaded program is executed while interacting with the user by using the input device 48 and the display device 50 and by using the RAM 36 as a work area. The processing routine of the jaw motion measuring program is described later.

<Method of Attaching Acceleration Detector>

(Method of Attaching to Chin Portion)

Figure 4A:
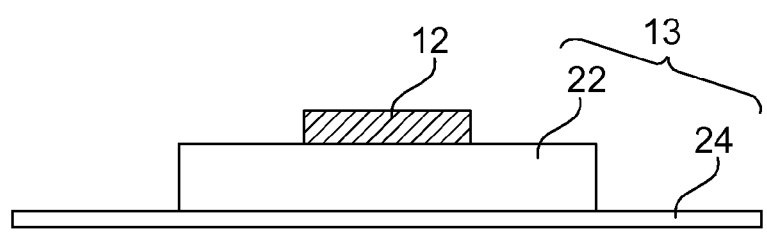
FIG. 4A is a layer sectional view showing the configuration of an attachment member.
Figure 4B:
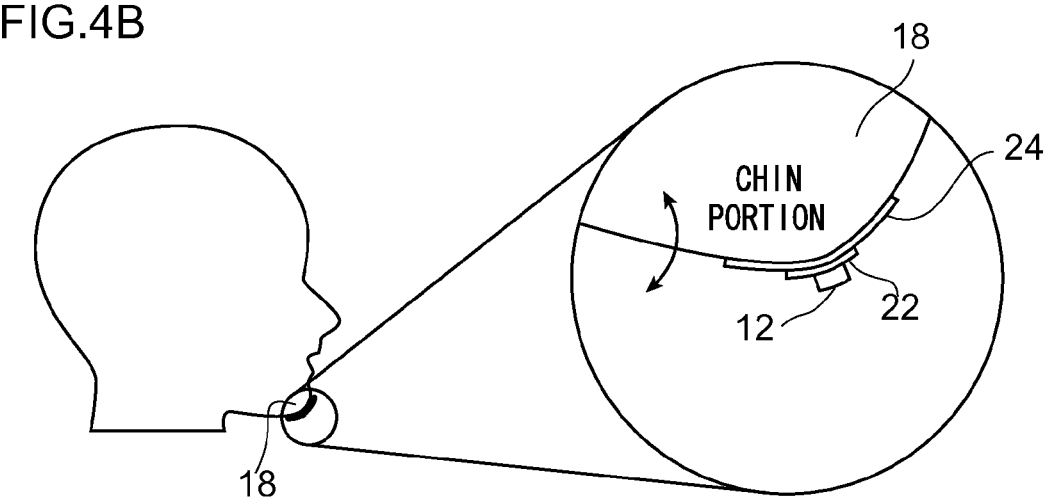
FIG. 4B is a schematic diagram showing a state in which the acceleration sensor is attached to a chin portion by the attachment member.

The method of attaching the acceleration detector is described next. FIG. 4A is a layer sectional view showing the configuration of an attachment member. FIG. 4B is a schematic diagram showing a state in which the acceleration sensor is attached to the chin portion 18 by the attachment member. Here, illustration of the flexible cable 14 and the like is omitted. As shown in FIG. 4A, the acceleration detector 10 has an attachment member 13 for attaching the acceleration sensor 12 to the chin portion 18 of the lower jaw.

The attachment member 13 has a buffer member 22 that holds the acceleration sensor 12 and absorbs vibrations of the skin, and an adhesive member 24 that adheres the acceleration sensor 12 to the chin portion 18 of the lower jaw via the buffer member 22. At the adhesive member 24 that is sheet-shaped, the surface, at the opposite side of the surface at which the buffer member 22 is provided, is the adhesive surface. A double-sided adhesive tape, that is somewhat thick at a thickness of around 1 mm, or the like, can be used as the buffer member 22. A medical adhesive tape, that has excellent adhesion to skin such as that used for electrocardiograph measurement, or the like, can be used as the adhesive member 24.

As shown in FIG. 4B, the attachment member 13 is attached by the adhesive surface of the adhesive member 24 being adhered to the skin of the chin portion 18 surface. The chin portion 18 is the distal end portion of the lower jaw and has a curved shape, but, by interposing the thick buffer member 22 between the acceleration sensor 12 and the adhesive member 24, not only are vibrations of the skin absorbed, but also, curving of the acceleration sensor 12 may be prevented.

(Relationship with Orthogonal Coordinate System of Acceleration Sensor)

Figure 5:
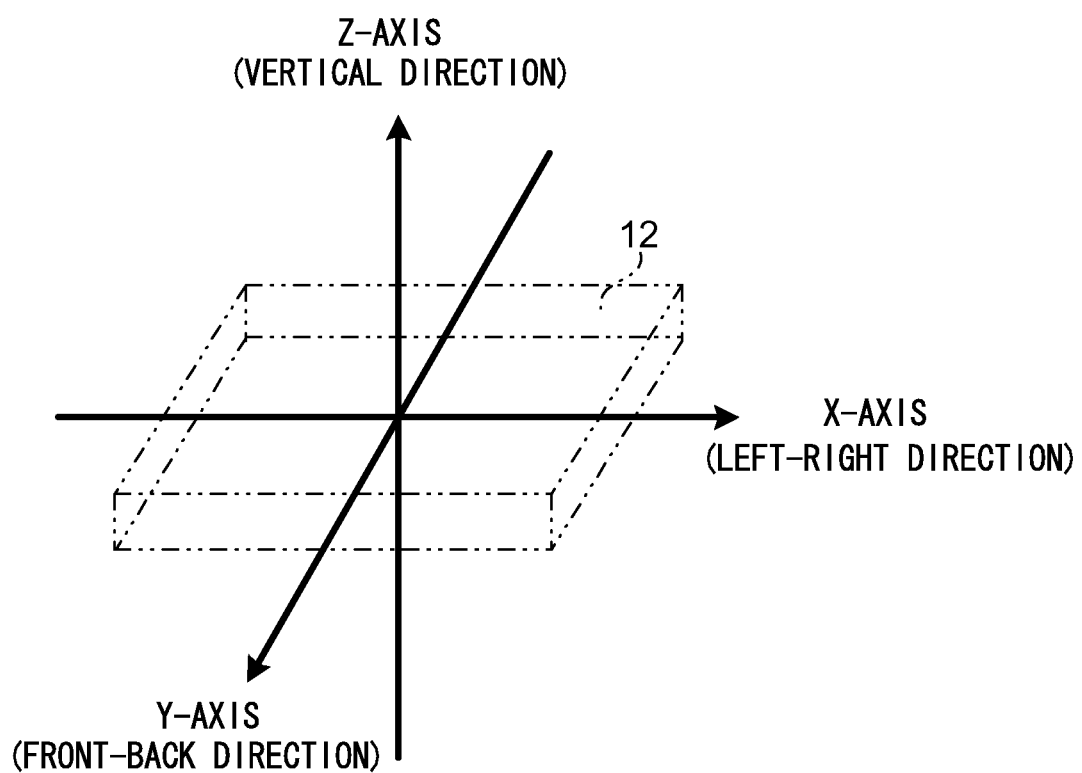
FIG. 5 is a drawing showing the relationship between an orthogonal coordinate system of the acceleration sensor and the directions of jaw motion.

FIG. 5 is a drawing showing the relationship between an orthogonal coordinate system of the acceleration sensor and the directions of jaw motion. The acceleration sensor 12 is a three-axis acceleration sensor that senses accelerations in the three-axis directions of the X-axis, the Y-axis and the Z-axis of an orthogonal coordinate system. There is a distinction between the left-right direction, the front-back direction, and the vertical direction at the chin portion 18 of the lower jaw that configures a portion of a human body. The acceleration sensor 12 is attached to the chin portion 18 of the lower jaw such that the X-axis direction corresponds to the left-right direction, the Y-axis direction corresponds to the front-back direction, and the Z-axis direction corresponds to the vertical direction. As described later with reference to the drawings, in more detail, the Y-axis direction corresponds to the tangent direction (the front-back direction) of rotating motion around the rotation axis of the mandibular condyle, and the Z-axis direction corresponds to the extending direction (the vertical direction) of a straight line that connects the aforementioned rotation axis and the acceleration sensor 12 (see FIG. 12).

Figure 6A:
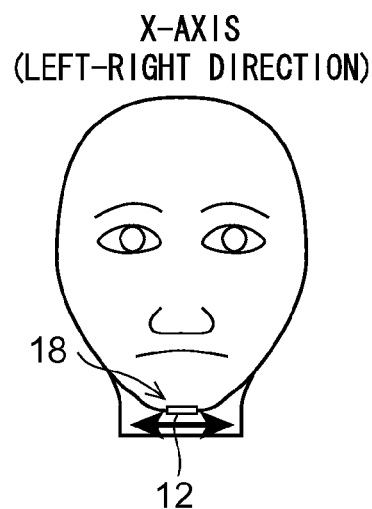
FIG. 6A is a drawing showing the left-right direction with respect to the chin portion of the lower jaw.
Figure 6B:
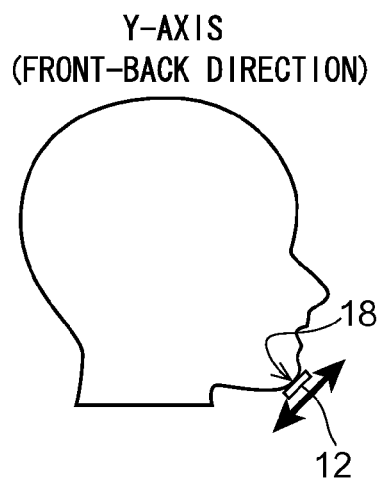
FIG. 6B is a drawing showing the front-back direction with respect to the chin portion of the lower jaw.
Figure 6C:
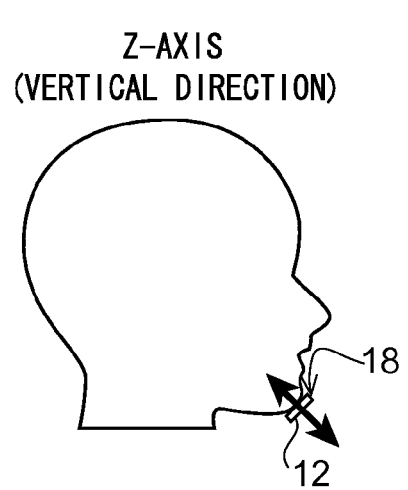
FIG. 6C is a drawing showing the vertical direction with respect to the chin portion of the lower jaw.

FIG. 6A, FIG. 6B and FIG. 6C are drawings showing the left-right direction, the front-back direction and the vertical direction with respect to the chin portion of the lower jaw. The acceleration sensor 12 is attached along the tangent line of the chin portion 18. As seen from the side, the acceleration sensor 12 is disposed so as to be inclined obliquely. The respective directions shown by the arrows correspond to the left-right direction, the front-back direction and the vertical direction with respect to the chin portion of the lower jaw. This is the correct attachment position, and, when the acceleration sensor 12 is attached at a position that is offset from this position, "position offset correction" that corrects the errors due to attachment position offset is needed, as described later.

<Attachment Position Offset Correction>
(Rotation Around Z-Axis, First Correction)

When the settings of the jaw motion measuring system that includes the acceleration detector 10, the interface device 20 and the jaw motion measuring device 30 are completed, and the attaching of the acceleration sensor 12 to the chin portion 18 of the subject by the attachment member 13 of the acceleration detector 10 is completed, input of acceleration data to the jaw motion measuring device 30 is started. Further, the jaw motion measuring device 30 starts-up the "jaw motion measuring program" that is stored in the ROM 34. FIG. 16 is a flowchart showing the processing routine of the jaw motion measuring program.

First, the subject is made to carry out a "tapping motion" in which the subject opens and closes the mouth and jaws at a substantially uniform interval. In step 100, the jaw motion measuring device 30 acquires the acceleration data of the time of tapping. In next step 102, a correction angle setting screen 60 shown in FIG. 7 is displayed on the display device 50 of the jaw motion measuring device 30.

Figure 7:
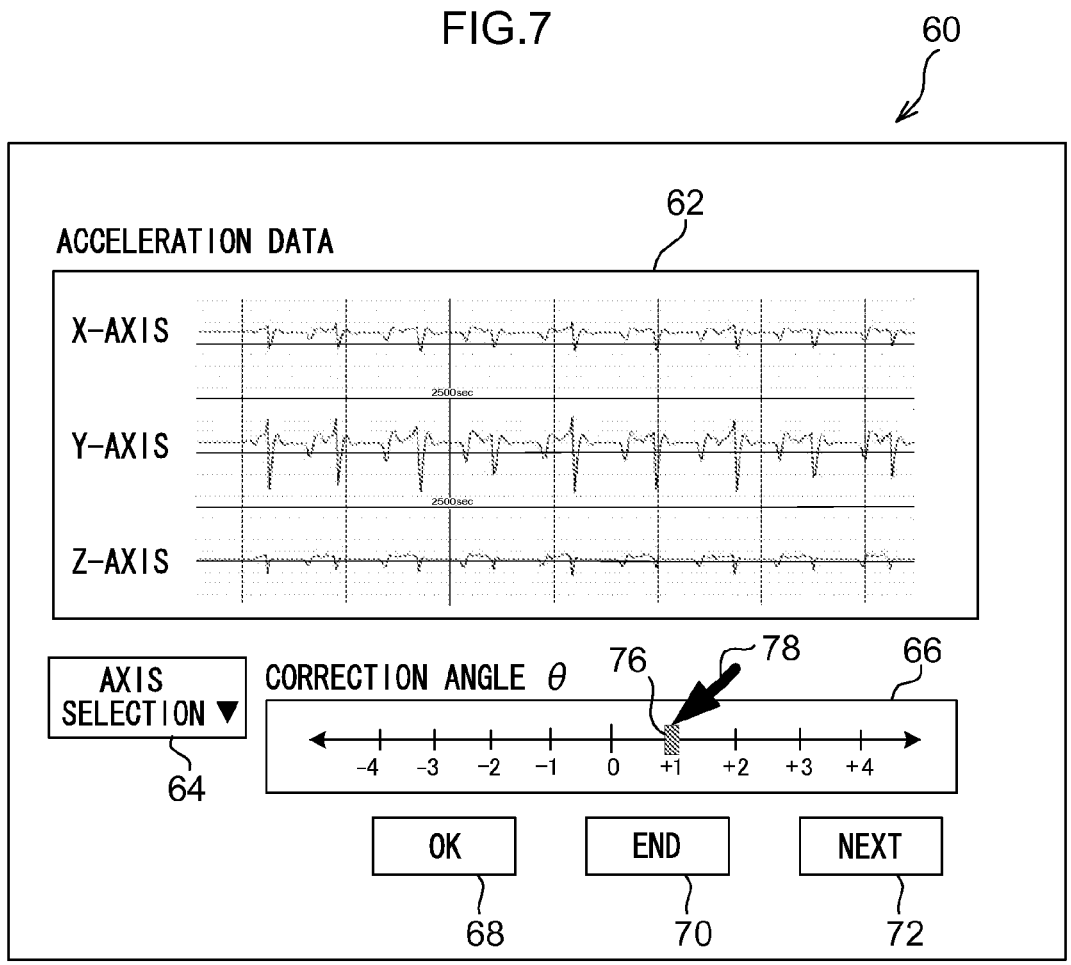
FIG. 7 is a drawing showing a correction angle setting screen.

As shown in FIG. 7, an acceleration data display section 62 that displays the acceleration data of the X-axis direction, the Y-axis direction and the Z-axis direction, an axis selection section 64, and an angle setting section 66 are displayed in the correction angle setting screen 60. The axis selection section 64 is configured such that any of the X-axis, the Y-axis and the Z-axis can be selected. The angle setting section 66 is configured such that a cursor 76 is moved by a pointer 78 on a scale from −4 to +4 for example, and a correction angle θ can be set. In addition thereto, an OK button 68, an end button 70, and a "next" button that instructs the next axis selection are displayed in the correction angle setting screen 60.

The operator looks at the acceleration data display section 62, and first confirms the acceleration data of the X-axis direction. When the operator judges that the amplitude of the acceleration data of the X-axis direction is large, the operator operates the axis selection section 64 and selects the Z-axis and sets correction angle $\theta_1$ around the Z-axis so that the amplitude of the acceleration data of the X-axis direction becomes the minimum (substantially zero), and selects the OK button 68.

At the jaw motion measuring device 30, in step 104, selection of the axis is confirmed, and when input of an OK instruction is confirmed in step 106, in next step 108, correction values of the acceleration data of the X-axis direction, the Y-axis direction and the Z-axis direction are computed on the basis of the set correction angle. Then, in step 110, the acceleration data after correction are displayed in the acceleration data display section 62 of the correction angle setting screen 60. As shown in FIG. 8, a data screen 62A is displayed in which the amplitude of the acceleration data of the X-axis direction has become substantially zero, and the amplitudes of the acceleration data of the Y-axis direction and the Z-axis direction have become large.

FIG. 9A and FIG. 9B are diagrams that explain the meaning of first correction. As shown in FIG. 9B, the first correction corresponds to a state in which, as seen from the acceleration sensor 12 side, at the chin portion 18, the acceleration sensor 12, that is attached with the X-axis direction inclined with respect to the left-right direction, is rotated such that the X-axis direction becomes parallel to the left-right direction. As shown in FIG. 9A, when viewed from the orthogonal coordinates side, the first correction corresponds to a state in which the orthogonal coordinates are rotated by the angle $\theta_1$ around the Z-axis. When this is expressed as a three-dimensional rotation matrix, it corresponds to coordinates (x, y, z) being transformed into coordinates (x', y', z') in accordance with following formula (1). Note that, in a rotation matrix in a three-dimensional coordinate, the forward direction of the rotation angle corresponds to the direction of a right screw. As a result, z'=z.

[Formula 1]

$$\begin{pmatrix} x' \\ y' \\ z' \end{pmatrix} = \begin{pmatrix} \cos\theta & -\sin\theta & 0 \\ \sin\theta & \cos\theta & 0 \\ 0 & 0 & 1 \end{pmatrix} \begin{pmatrix} x \\ y \\ z \end{pmatrix} \quad (1)$$

(Rotation Around X-Axis, Second Correction)

The operator looks at the acceleration data display section 62 in which the data screen 62A after correction is displayed, and confirms the acceleration data of the Z-axis direction. When the operator judges that the amplitude of the acceleration data of the Z-axis direction is large, the operator operates the "next" button 72 and selects the next axis. When the amplitude of the acceleration data of the Z-axis direction is appropriate, the operator operates the end button 70, and the position offset correction is ended.

When selection of a "next" instruction is confirmed in step 112, the jaw motion measuring device 30 returns to step 102, and the correction angle setting screen 60 shown in FIG. 7 is displayed on the display device 50 of the jaw motion measuring device 30.

The operator operates the axis selection section 64 and selects the X-axis and sets correction angle $\theta_2$ around the X-axis so that the amplitude of the acceleration data of the Z-axis direction becomes the minimum (substantially zero), and selects the OK button 68. Due to this second correction, the Y-axis direction corresponds to the tangent direction (the front-back direction) of rotation motion around the rotation axis of the mandibular condyle, and the Z-axis direction corresponds to the extending direction (the vertical direction) of the straight line that connects that rotation axis and the acceleration sensor 12 (see FIG. 12).

Figure 10:
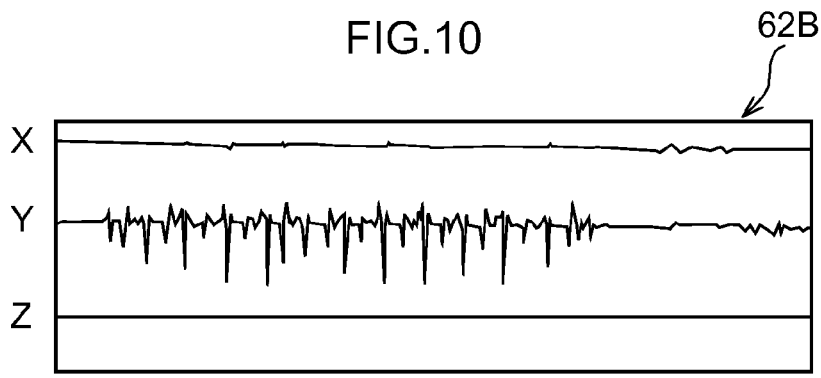
FIG. 10 is a drawing showing a screen that displays acceleration data after correction.

In the same way as in steps 104 through 110, on the basis of the set correction angle, the jaw motion measuring device 30 computes the correction values of the acceleration data of the X-axis direction, the Y-axis direction and the Z-axis direction, and displays the acceleration data after correction in the acceleration data display section 62 of the correction angle setting screen 60. As shown in FIG. 10, a data screen 62B is displayed in which the amplitude of the acceleration data of the Z-axis direction has become small, and the amplitude of the acceleration data of the Y-axis direction has become large.

Figure 12A:
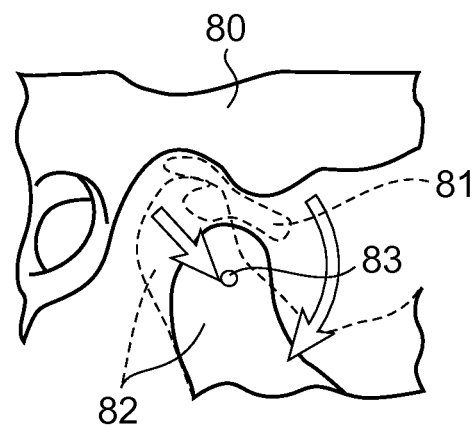
FIG. 12A is an explanatory drawing that explains the relationship between jaw motion and an attached position of the acceleration sensor.
Figure 12B:
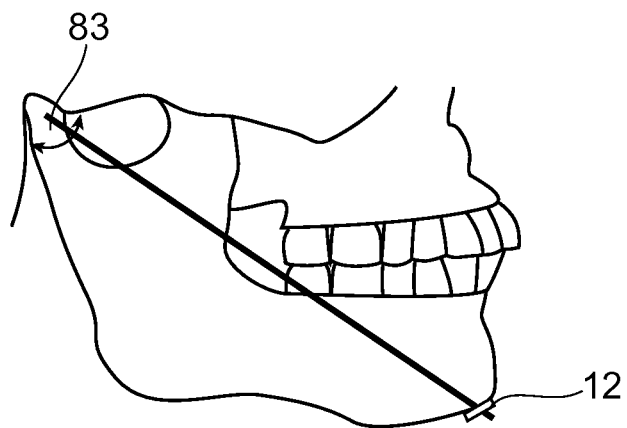
FIG. 12B is an explanatory drawing that explains the relationship between jaw motion and the attached position of the acceleration sensor.

FIG. 12A and FIG. 12B are explanatory drawings that explain the relationship between jaw motion and the attached position of the acceleration sensor. As shown by the arrows in FIG. 12A, jaw motion is classified into "rotating motion" around a rotation axis 83 of a mandibular condyle 82 with a mandibular fossa 80 being a bearing, and "gliding motion" in which the mandibular condyle 82 moves forward with respect to the mandibular fossa 80. Note that cartilage 81 is interposed between the mandibular fossa 80 and the mandibular condyle 82. As shown by the thick solid line in FIG. 12B, the acceleration sensor 12 is attached to the chin portion 18 of the lower jaw such that the Y-axis direction corresponds to the tangent direction (the front-back direction) of the rotation motion around the rotation axis of the mandibular condyle, and the Z-axis direction corresponds to the extending direction (the vertical direction) of the straight line that connects that rotation axis and the acceleration sensor 12.

Accordingly, in the case of "gliding motion (simultaneous left and right)" in which the mandibular condyle 82 moves forward simultaneously at the left and the right, movement in the vertical direction (corresponding to the Z-axis direction) with respect to the chin portion of the lower jaw is applied (see FIG. 6C). In the case of "gliding motion (left-right displacement)" in which the mandibular condyle 82 moves forward separately at the left and the right, movement in the left-right direction (corresponding to the X-axis direction) with respect to the chin portion of the lower jaw is applied (see FIG. 6A).

The "tapping motion" in which the mouth or jaw is opened and closed at a substantially uniform interval is basically the rotation motion shown in FIG. 12A, and the movement in the front-back direction (corresponding to the Y-axis direction) with respect to the chin portion of the lower jaw is the greatest (see FIG. 6B). Accordingly, in the present embodiment, the tapping motion is measured, and correction is carried out such that the amplitudes of the acceleration data of the X-axis direction and the Z-axis direction become small (in other words, so that the amplitude of the acceleration data of the Y-axis direction becomes large).

Figure 11A:
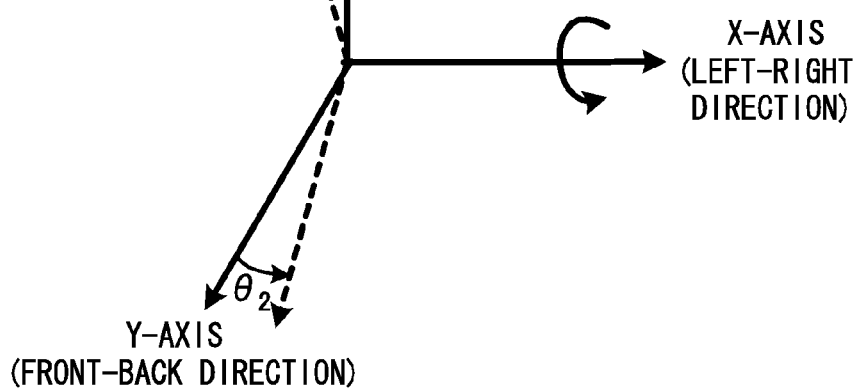
FIG. 11A is a drawing that explains the meaning of second correction.
Figure 11B:
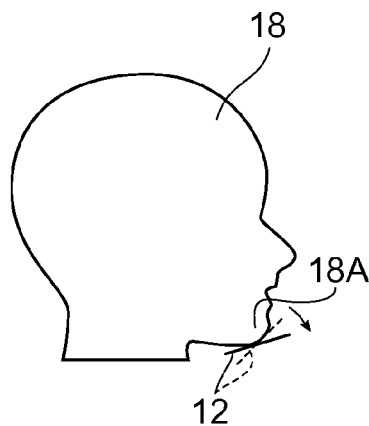
FIG. 11B is a drawing that explains the meaning of second correction.

FIG. 11A and FIG. 11B are drawings that explain the meaning of the second correction. As shown in FIG. 11B, the second correction corresponds to a state in which, as seen from the acceleration sensor 12 side, at the chin portion 18, the acceleration sensor 12, that is attached with the Z-axis direction inclined with respect to the vertical direction, is rotated around the X-axis direction (left-right direction) such that the Z-axis direction becomes parallel to the vertical direction. As shown in FIG. 11A, when viewed from the orthogonal coordinates side, the second correction corresponds to a state in which the orthogonal coordinates are rotated by the angle $\theta_2$ around the X-axis. When this is expressed as a three-dimensional rotation matrix, it corresponds to coordinates (x', y', z') being transformed into coordinates (x", y", z") in accordance with following formula (2). As a result, x"=x'.

[Formula 2]

$$\begin{pmatrix} x'' \\ y'' \\ z'' \end{pmatrix} = \begin{pmatrix} 1 & 0 & 0 \\ 0 & \cos\theta & -\sin\theta \\ 0 & \sin\theta & \cos\theta \end{pmatrix} \begin{pmatrix} x' \\ y' \\ z \end{pmatrix} \quad (2)$$

The operator looks at the acceleration data display section 62 in which the data screen 62B after correction is displayed, and confirms the acceleration data of the X-axis direction, the Y-axis direction ad the Z-axis direction. When the amplitudes of the acceleration data of the respective axis directions are appropriate, the operator operates the end button 70 and ends the position offset correction.

<Base Line Setting>

Figure 13:
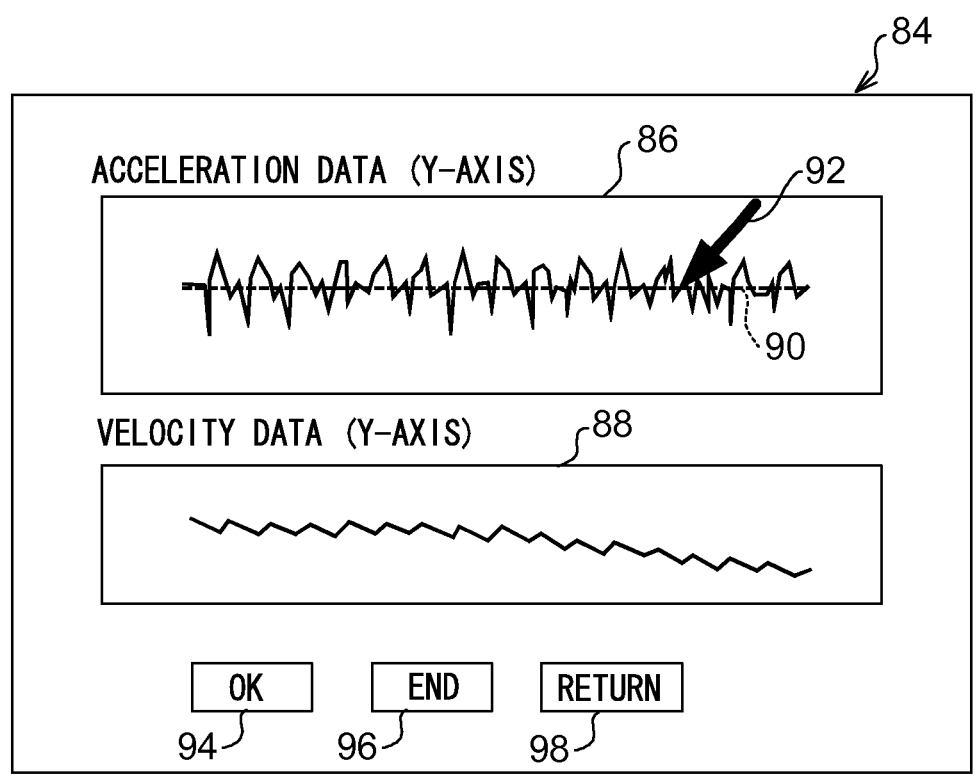
FIG. 13 is a drawing showing a base line setting screen.

When selection of an end instruction is confirmed in step 114, the jaw motion measuring device 30 proceeds to step 116, and displays a base line setting screen 84 shown in FIG. 13 on the display device 50 of the jaw motion measuring device 30. An acceleration data display section 86 that displays the acceleration data of the Y-axis direction, and a velocity data display section 88 that displays velocity data that is obtained by integrating the acceleration data of the Y-axis direction, are displayed in the base line setting screen 84.

As shown by the dashed line, a base line setting line 90 for setting the position of the base line is displayed in the acceleration data display section 86. The base line setting line 90 is moved up and down by a pointer 92, and is configured so as to be able to set the position of the base line. In addition, an OK button 94, an end button 96, and a "return" button 98 that instructs returning to setting of the base line, are displayed in the base line setting screen 84.

The operator moves the base line setting line 90 and sets it at a predetermined position, and selects the OK button 94.

When input of an OK instruction is confirmed in step 118, in the next step 120, the jaw motion measuring device 30, on the basis of the set base line, integrates the acceleration data of the Y-axis direction, and computes the velocity data of the Y-axis direction. Then, in step 122, the velocity data after base line setting is displayed in the velocity data displaying section 88 of the base line setting screen 84.

FIG. 14A, FIG. 14B and FIG. 14C are drawings showing relationships between the position of the base line and a velocity waveform. The acceleration data is obtained as a voltage signal that is proportional to the acceleration, and the zero point is not prescribed. Accordingly, even when this is integrated and the velocity is determined, a correct value cannot be obtained. As shown in FIG. 14A, when the position of the base line is high, the velocity waveform falls toward the right. In contrast, as shown in FIG. 14C, when the position of the base line is low, the velocity waveform rises toward the right. These both show that the position of the base line (i.e., the zero point of the acceleration waveform) is not appropriate. On the other hand, as shown in FIG. 14B, if the velocity waveform can be made to be flat so as to fluctuate in a definite amplitude range, the position of the base line is set appropriately.

The operator looks at the display of the velocity data displaying section 88, and, until the position of the base line becomes appropriate, selects the "return" button 98 and repeatedly carries out setting of the base line. Then, when the position of the base line becomes appropriate, the operator selects the "end" button 96, and decides upon the base line.

When input of a "return" instruction is confirmed in step 124, the jaw motion measuring device 30 returns to step 116, and displays the base line setting screen 84, and, in the same way as in steps 118 through 122, computes the velocity data of the Y-axis direction on the basis of the set base line, and displays the velocity data after base line setting. On the other hand, in step 126, when input of an end instruction is confirmed, the jaw motion measuring device 30 proceeds to step 128.

Figure 15:
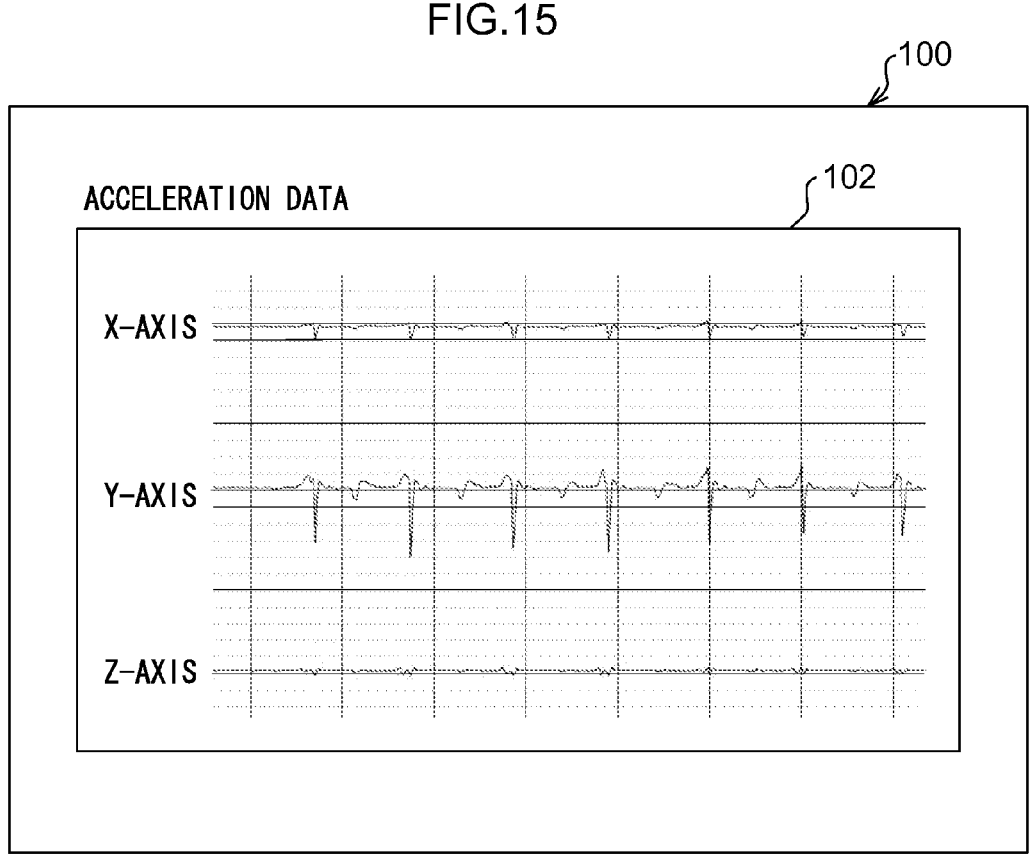
FIG. 15 is a drawing showing a jaw motion measurement screen.

In step 128, a jaw motion measurement screen 100, that includes acceleration data 102 that is displayed on the basis of the base lines that were finally set, is displayed as shown in FIG. 15. Namely, the acceleration waveforms of the X-axis direction, the Y-axis direction and the Z-axis direction are displayed together with the zero points (base lines) of the acceleration waveforms. This is a screen that shows accurate measurement results of the jaw motion. This jaw motion measurement screen 100 is displayed, and the processing routine of the jaw motion measuring program ends.

As described above, in accordance with the present embodiment, a simple detector equipped with a three-axis acceleration sensor is attached, and simultaneously, "position offset correction" that corrects errors due to attached position offset of the acceleration sensor and "base line setting" that prescribes the zero point of the acceleration waveform are carried out, and measurement of jaw motion may be carried out accurately.

Further, in accordance with the present embodiment, while looking at the subject as well as the display screen, the "position offset correction" and "base line setting" may be carried out in real time.

Further, in accordance with the present embodiment, the generation of noise due to vibrations of the acceleration sensor may be suppressed by structuring the detector, that is equipped with the three-axis acceleration sensor, by using a light-weight and compact acceleration sensor, a light-weight and highly-flexible flexible wire, a buffer member that holds the acceleration sensor and absorbs vibrations of the skin, and the like.

Moreover, by making it possible to accurately measure jaw motion by a simple device configuration as described above, various applications may be possible. For example, application to a diagnosing system of early stage contact, such as occlusion diagnosis or the like, may be possible. Further, measuring (, computing) the smoothness (i.e., the value obtained by time-differentiating the acceleration) of the jaw motion is related also to proposals of new parameters for evaluating chewing motion. Further, by making the system light-weight and cordless, measurement of the eating situation and the conversation and the like of a care-receiver may also be possible, and QOL (Quarity of Life) being quantified as an objective numerical value is anticipated. Further, application as a decisive diagnosing device of the Tooth Contacting Habit (the habit of regularly causing the teeth of the upper and lower jaws to contact), that is thought to be a direct cause of tension headaches and uncomfortable feeling of the occlusion for which the number of patients is increasing in recent years, may also be possible.

Note that the above-described embodiment describes an example, in which the "base line setting" is carried out after the "position offset correction, but there are also cases in which the "position offset correction" is carried out after the "base line setting". Further, an example is described in which "rotation around the X-axis (second correction)" is carried out after "rotation around the Z-axis (first correction)", but the "rotation around the Z-axis (first correction)" may be carried out after the "rotation around the X-axis (second correction)".

Further, the above-described embodiment describes an example in which the acceleration sensor is wire-connected to the jaw motion measuring device that is configured by a computer or the like, but an acceleration sensor at which wireless communication is possible also can be used, provided that it is a light-weight and compact acceleration sensor. In this case, wireless signals from the acceleration sensor are inputted to the communication I/F of the jaw motion measuring device.

The invention claimed is:

1. A jaw motion measuring system comprising:
an acceleration detector having at least an acceleration sensor that senses accelerations of three-axis directions, a flexible wire that is configured by a plurality of thin wires covered by insulating covering films being bundled together and that is light-weight and provided with flexibility to an extent of not causing accelerations sensed by the acceleration sensor to fluctuate and whose one end is connected to the acceleration sensor, an output terminal that is connected to another end of the flexible wire and outputs acceleration data of the three-axis directions, and an attachment portion that attaches the acceleration sensor to a chin portion of a lower jaw; and a jaw motion measuring device that acquires acceleration data corresponding to jaw motion from the acceleration detector, and carries out correction, with respect to the acquired acceleration data, of errors due to the acceleration sensor, and measures jaw motion expressed by acceleration waveforms, wherein, given that an X-axis direction of the acceleration sensor is made to correspond to a left-right direction of the chin portion of the lower jaw, a Y-axis direction is made to correspond to a front-back direction that is a tangent line direction of rotational motion around a rotation axis of a mandibular condyle, and a Z-axis direction is made to correspond to a vertical direction that is an extending direction of a straight line that connects the rotation axis and the acceleration sensor, the jaw motion measuring device has a position offset correcting unit that carries out a first correction, that rotates orthogonal coordinates of the acceleration sensor around a Z-axis such that acceleration data of the X-axis direction becomes a minimum, and a second correction, that rotates the orthogonal coordinates of the acceleration sensor around an X-axis such that acceleration data of the Z-axis direction becomes a minimum, and carries out correction, with respect to the acquired acceleration data, of errors due to attachment position offset of the acceleration sensor.

2. The jaw motion measuring system claim 1, wherein the jaw motion measuring device further has a display device and a display control device that controls the display device, and the display control device displays, on the display 18 device, acceleration data acquired from the acceleration detector, an axis selection section that selects any of three axes of the acceleration sensor, and an angle setting section that sets a rotation angle around a selected axis, and the position offset correcting unit carries out first correction, that rotates the orthogonal coordinates of the acceleration sensor around the Z-axis selected by the axis selecting section by an angle set by the angle setting section and makes the acceleration data of the X-axis direction be the minimum, and second correction, that rotates the orthogonal coordinates of the acceleration sensor around the X-axis selected by the axis selecting section by an angle set by the angle setting section and makes the acceleration data of the Z-axis direction be the minimum.

3. The jaw motion measuring system of claim 1, wherein the jaw motion measuring device further has a base line setting unit that sets a base line for acceleration data acquired from the acceleration detector and prescribes a zero point of an acceleration waveform, so that a velocity waveform, that is obtained by integrating a voltage signal of the Y-axis direction, fluctuates in a definite amplitude range.

4. The jaw motion measuring system of claim 3, wherein, until a base line is decided upon, the jaw motion measuring device repeatedly carries out a first process, in which the display control device displays, on the display device, acceleration data of the Y-axis direction acquired from the acceleration detector and a base line setting section that sets a base line for the acquired acceleration data, and a second process in which the base line setting unit integrates the acceleration data of the Y-axis direction on the basis of a base line set by the base line setting section, and a third process in which the display control device displays, on the display device, a velocity waveform obtained by integrating the acceleration data of the Y-axis direction, and the jaw motion measuring device sets a base line for the acceleration data, and prescribes a zero point of an acceleration waveform.

5. The jaw motion measuring system of claim 1, wherein the acceleration sensor is made to be light-weight and compact, to an extent that skin of the chin portion of the lower jaw is not made to hang downward.

6. The jaw motion measuring system of claim 1, wherein the attachment portion has a buffer member that holds the acceleration sensor and absorbs vibrations of skin and prevents curving of the acceleration sensor, and an adhering member that adheres the acceleration sensor to the chin portion of the lower jaw via the buffer member.

* * * * *